(12) United States Patent
Dubief et al.

(10) Patent No.: US 7,232,561 B2
(45) Date of Patent: *Jun. 19, 2007

(54) WASHING COMPOSITIONS COMPRISING AT LEAST ONE AMPHIPHILIC BLOCK COPOLYMER AND AT LEAST ONE CATIONIC OR AMPHOTERIC POLYMER

(75) Inventors: Claude Dubief, Le Chesnay (FR); Serge Restle, Saint-Prix (FR); Franck Giroud, Clichy (FR)

(73) Assignee: L'Oreal S.A., Paris (FR)

( * ) Notice: Subject to any disclaimer, the term of this patent is extended or adjusted under 35 U.S.C. 154(b) by 288 days.

This patent is subject to a terminal disclaimer.

(21) Appl. No.: 10/449,119

(22) Filed: Jun. 2, 2003

(65) Prior Publication Data

US 2004/0039101 A1   Feb. 26, 2004

Related U.S. Application Data

(60) Provisional application No. 60/385,565, filed on Jun. 5, 2002.

(30) Foreign Application Priority Data

May 31, 2002   (FR) .................................. 02 06731

(51) Int. Cl.
- *A61K 8/72* (2006.01)
- *A61K 8/90* (2006.01)
- *C11D 1/86* (2006.01)
- *C11D 3/37* (2006.01)
- *C11D 1/02* (2006.01)

(52) U.S. Cl. ................ 424/70.11; 424/70.5; 424/70.15; 424/70.16; 424/70.19; 424/70.22; 510/123; 510/125; 510/130; 510/391; 510/426; 510/475; 510/492

(58) Field of Classification Search ................ 510/123, 510/125, 130, 391, 426, 475, 492; 424/70.5, 424/70.11, 70.15, 70.16, 70.19, 70.22
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,528,378 A | 11/1950 | Mannheimer |
| 2,781,354 A | 2/1957 | Mannheimer |
| 2,961,347 A | 11/1960 | Floyd |
| 3,206,462 A | 9/1965 | McCarty |
| 3,227,615 A | 1/1966 | Korden |
| 3,632,559 A | 1/1972 | Matter et al. |
| 3,874,870 A | 4/1975 | Green et al. |
| 3,907,984 A | 9/1975 | Calvert et al. |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,131,576 A | 12/1978 | Iovine et al. |
| 4,172,887 A | 10/1979 | Vanlerberghe et al. |
| 4,223,009 A | 9/1980 | Chakrabarti |
| 4,277,581 A | 7/1981 | Vanlerberghe et al. |
| 4,349,532 A | 9/1982 | Vanlerberghe et al. |
| 4,591,610 A | 5/1986 | Grollier |
| 4,608,250 A | 8/1986 | Jacquet et al. |

(Continued)

FOREIGN PATENT DOCUMENTS

EP          0 337 354        10/1989

(Continued)

OTHER PUBLICATIONS

Craig J. Hawker, "Advances in 'Living' Free-radical Polymerization: Architectural and Structural Control," Trends in Polymer Science, vol. 4, No. 6, Jun. 1996, pp. 183-188.

(Continued)

*Primary Examiner*—Brian Mruk
(74) *Attorney, Agent, or Firm*—Finnegan, Henderson, Farabow, Garrett & Dunner, L.L.P.

(57) ABSTRACT

A composition for washing a keratinous substance comprising, in a cosmetically acceptable aqueous or aqueous/alcoholic medium,
- at least one linear block copolymer comprising at least one hydrophobic block and at least one hydrophilic block, with the exception of block copolymers of ethylene oxide and of propylene oxide, block copolymers comprising urethane units and block copolymers comprising siloxane units,
- at least one polymer chosen from cationic and amphoteric polymers, and
- at least one anionic surface-active agent in combination with at least one additional surface-active agent chosen from nonionic surface-active agents and amphoteric surface-active agents,
- and a method for washing keratinous substances, for example, keratinous fibers using said composition.

31 Claims, No Drawings

U.S. PATENT DOCUMENTS

| | | | |
|---|---|---|---|
| 4,719,099 A | 1/1988 | Grollier et al. | |
| 4,761,273 A | 8/1988 | Grollier et al. | |
| 4,839,166 A | 6/1989 | Grollier et al. | |
| 5,139,037 A | 8/1992 | Grollier et al. | |
| 5,196,189 A | 3/1993 | Jacquet et al. | |
| 5,324,765 A | 6/1994 | Mondet et al. | |
| 5,958,392 A | 9/1999 | Grollier et al. | |
| 6,383,994 B1 * | 5/2002 | Maurin et al. | 510/119 |
| 6,403,542 B1 | 6/2002 | Maurin et al. | |

FOREIGN PATENT DOCUMENTS

| | | |
|---|---|---|
| EP | 0 494 022 A1 | 7/1992 |
| EP | 0 943 627 | 9/1999 |
| EP | 1 092 420 A1 | 4/2001 |
| FR | 1 492 597 | 8/1967 |
| FR | 1 583 363 | 10/1969 |
| FR | 2 077 143 | 10/1971 |
| FR | 2 080 759 | 11/1971 |
| FR | 2 162 025 | 7/1973 |
| FR | 2 190 406 | 2/1974 |
| FR | 2 252 840 | 6/1975 |
| FR | 2 270 846 | 12/1975 |
| FR | 2 280 361 | 2/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 383 660 | 10/1978 |
| FR | 2 393 573 | 1/1979 |
| FR | 2 413 907 | 8/1979 |
| FR | 2 470 596 | 6/1981 |
| FR | 2 505 348 | 11/1982 |
| FR | 2 519 863 | 7/1983 |
| FR | 2 542 997 | 9/1984 |
| FR | 2 598 611 | 11/1987 |
| FR | 2 709 954 | 3/1995 |
| WO | WO 90/03779 | 4/1990 |
| WO | WO 01/96429 A1 | 12/2001 |

OTHER PUBLICATIONS

Jin-Shan Wang et al., "Controlled/'Living' Radical Polymerization. Atom Transfer Radical Polymerization in the Presence of Transition-Metal Complexes," J. Am. Chem. Soc., vol. 117, 1995, pp. 5614-5615.

Michael K. Georges et al., "Narrow Molecular Weight Resins by a Free-Radical Polymerization Process," Macromolecules, vol. 26, 1993, pp. 2987-2988.

M.R. Porter, BSc, PhD. CChem, MRSC, "Handbook of Surfactants," Blackie & Son Ltd., Glasgow and London, 1991, pp. 116-178.

English language Derwent Abstract of 2 077 143, Oct. 15, 1971.
English language Derwent Abstract of FR 2 080 759, Nov. 19, 1971.
English language Derwent Abstract of FR 2 320 330, Mar. 4, 1977.
English language Derwent Abstract of 2 336 434, Jul. 11, 1977.
English language Derwent Abstract of FR 2 709 954, Mar. 24, 1995.

* cited by examiner

WASHING COMPOSITIONS COMPRISING AT LEAST ONE AMPHIPHILIC BLOCK COPOLYMER AND AT LEAST ONE CATIONIC OR AMPHOTERIC POLYMER

This application claims benefit of U.S. Provisional Application No. 60/385,565 filed Jun. 5, 2002.

Disclosed herein are foaming and detergent compositions, intended to wash, condition and style hair, comprising at least one amphiphilic block copolymer and at least one polymer chosen from cationic and amphoteric polymers.

Cationic polymers are by far most widely used in shampoos for facilitating disentangling of wet hair and improving its softness after drying. However, these polymers may exhibit a mediocre styling power and may not make it possible to give body to the hair.

The combination of such cationic conditioning polymers with anionic fixing polymers can result in an improvement in the styling performance of shampoos (body and form retention) but may unfavorably alter the feel of the hair by rendering it dry and rough.

The use of silicones or of a mixture of silicones and of cationic polymers in styling shampoos can provide good disentangling of the hair but may confer on it an excessively silky feel which may not be desired for such styling shampoos.

Block copolymers comprising silicone blocks, used alone or in combination with cationic polymers, can facilitate the disentangling and can improve the styling power of shampoos but also can give an excessively silky feel.

Polyurethanes comprising polyester or polyether blocks, optionally in combination with cationic film-forming polymers, for their part can result in a waxy, sometimes sticky, feel.

Block copolymers of ethylene oxide and of propylene oxide can have virtually no beneficial effect on the hair.

The inventors have surprisingly discovered that the use of a cationic polymer in combination with an amphiphilic linear block copolymer in a specific base for washing compositions, such as shampoos, can make it possible to obtain products with at least one of the following effects: improving the disentangling of the hair in the wet state; giving body to dried hair; and facilitating the shaping of the hairstyle and the form retention of the latter without detrimentally affecting the smooth and glossy appearance and the pleasant touch of the treated hair.

Disclosed herein is a composition for washing a keratinous substance, for example, keratinous fibers, comprising, in a cosmetically acceptable aqueous or aqueous/alcoholic medium, at least one linear block copolymer comprising at least one hydrophobic block and at least one hydrophilic block, with the exception of block copolymers of ethylene oxide and of propylene oxide, block copolymers comprising urethane units and block copolymers comprising siloxane units, at least one polymer chosen from cationic and amphoteric polymers, and at least one anionic surface-active agent in combination with at least one additional surface-active agent chosen from nonionic surface-active agents and amphoteric surface-active agents.

Further disclosed herein is the use of such a composition for washing a keratinous substance, for example, keratinous fibers.

The at least one linear block copolymer which can be used in the compositions disclosed herein is an "amphiphilic" copolymer, i.e., a copolymer comprising both hydrophobic blocks and hydrophilic blocks.

As used herein, the term "hydrophobic blocks" means blocks comprising at least 75 mol % of water-insoluble monomers and the term "hydrophilic blocks" means blocks comprising at least 75 mol % of water-soluble monomers.

As used herein, a "water-soluble" monomer is a monomer which, when it is introduced into water at a temperature of 25° C. and at a concentration by weight of 0.5%, optionally neutralized, makes it possible to obtain a macroscopically homogeneous and transparent solution, i.e., having a light transmission value, at a wavelength of 500 nm, through a sample with a thickness of 1 cm, for example, of at least 70%, further, for example, of at least 80%.

The water-soluble monomers forming the at least one hydrophilic block of the at least one linear block copolymer used herein can be chosen from monomers of anionic, nonionic and cationic nature and can be used alone or in the form of a mixture comprising two or more different monomers.

For example, the anionic water-soluble monomers may be chosen from monomers of carboxylic acids comprising ethylenic unsaturation, such as acrylic acid, methacrylic acid, itaconic acid, fumaric acid, crotonic acid and maleic acid, 2-acrylamido-2-methylpropanesulfonic acid, styrenesulfonic acid, vinylsulfonic acid and vinylphosphonic acid.

The nonionic water-soluble monomers may, for example, be chosen from acrylamides, N-($C_{1-6}$ alkylated)acrylamides and N,N-di($C_{1-3}$ alkylated)acrylamides, polyethylene glycol acrylate, polyethylene glycol methacrylate, N-vinylacetamide, N-methyl-N-vinylacetamide, N-vinylformamide, N-methyl-N-vinylformamide, N-vinyllactams comprising at least one cyclic group chosen from cyclic groups comprising from 4 to 9 carbon atoms, vinyl alcohol (copolymerized in the form of vinyl acetate and then hydrolyzed), ethylene oxide, hydroxyethyl acrylate, hydroxypropyl acrylate, hydroxyethyl methacrylate and hydroxypropyl methacrylate.

The cationic water-soluble monomers may, for example, be chosen from dimethyldiallylammonium chloride, methylvinylimidazolium chloride, 2-vinylpyridine, 4-vinylpyridine, 2-methyl-5-vinylpyridine, N-($C_{1-4}$ alkyl)-4-vinylpyridinium halides, such as N-methyl-4-vinylpyridinium iodide, vinylamine and monomers of the following formula:

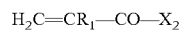

$$H_2C=CR_1-CO-X_2$$

wherein:

$R_1$ is chosen from a hydrogen atom and a methyl group;

$X_2$ is chosen from linear and branched $C_{1-6}$ hydrocarbonaceous groups carrying at least one entity chosen from primary, secondary and tertiary amine functional groups; quaternary nitrogen atoms; groups of formula $NHR_2$; and groups of formula $NR_2R_3$, wherein $R_2$ and $R_3$, which may be identical or different, can each be chosen from linear and branched $C_{1-6}$ hydrocarbonaceous groups carrying at least one entity chosen from primary, secondary and tertiary amine functional groups and quaternary nitrogen atoms.

The water-insoluble monomers forming the at least one hydrophobic block of the at least one linear block copolymer disclosed herein can, for example, be chosen from vinylaromatic monomers, such as styrene and its alkylated derivatives, for example, 4-butylstyrene, α-methylstyrene and vinyltoluene; dienes, such as butadiene and 1,3-hexadiene; alkylated derivatives of dienes, such as isoprene and dimethylbutadiene; chloroprene; $C_{1-10}$ alkyl, $C_{6-10}$ aryl and $C_{7-20}$ aralkyl acrylates; $C_{1-10}$ alkyl, $C_{6-10}$ aryl and $C_{7-20}$ aralkyl methacrylates, for example, methyl, ethyl, n-butyl, 2-ethylhexyl, tert-butyl, isobornyl, phenyl and benzyl (meth) acrylates; vinyl acetate; vinyl ethers of formula $CH_2$=CH—O—R and allyl ethers of formula $CH_2$=CH—$CH_2$—O—R wherein R is chosen from $C_{1-6}$ alkyl groups; acrylonitrile; vinyl chloride; vinylidene chloride; caprolactone; ethylene, propylene, and fluorinated vinyl monomers; and vinyl monomers comprising at least one perfluorinated chain, such as fluoroalkyl acrylates and methacrylates and alkyl α-fluoroacrylates.

As indicated above with respect to the definition of the hydrophobic and hydrophilic blocks of the block copolymers, the water-insoluble monomers and the water-soluble monomers represent at least 75 mol % respectively of the hydrophobic and hydrophilic blocks. In other words, each hydrophobic block can comprise up to 25 mol % of at least one water-soluble monomer. This proportion may, for example, be at most equal to 10 mol % and further, for example, may be less than or equal to 5 mol %.

Similarly, each hydrophilic block can comprise, for example, up to 25 mol %, and further, for example, up to 10 mol % and even further, for example, up to 5 mol % of at least one water-insoluble monomer.

The at least one linear block copolymer disclosed herein can also, for example, be chosen from copolymers wherein the at least one hydrophilic block and the at least one hydrophobic block are composed exclusively of water-soluble monomers and of water-insoluble monomers respectively. The at least one hydrophilic block and the at least one hydrophobic block can be chosen from homopolymer blocks and copolymer blocks comprising at least two different monomers of the same type.

The number-average molecular mass of each block, whether hydrophobic or hydrophilic or copolymer or homopolymer, can range, for example, from 500 to 100 000, and further, for example, from 500 to 50 000, with a polydispersity index ($M_w/M_n$) ranging, for example, from 1.01 to 3.0, and further, for example, from 1.1 to 2.5.

The at least one linear block copolymer disclosed herein can be chosen, for example, from:
diblock copolymers of formula AB,
triblock copolymers of formulae ABA and BAB, and
multiblock copolymers comprising at least two hydrophilic blocks and at least two hydrophobic blocks arranged alternately, wherein A is the at least one hydrophilic block and B is the at least one hydrophobic block, and it is possible for the blocks A of the same polymer to be identical or different and it is possible for the blocks B of the same polymer to be identical or different.

For example, the at least one linear block copolymer can be chosen from diblock copolymers and triblock copolymers comprising a hydrophilic central block and two hydrophobic side blocks The washing compositions, such as shampoos, disclosed herein may, for example, comprise the at least one linear block copolymer in a dissolved or finely dispersed state, in other words, the at least one linear block copolymer may, for example, be soluble or finely dispersible in the cosmetically acceptable medium.

As used herein, the term "soluble" or "finely dispersible" in a given medium means that polymers which, introduced into such a medium at a temperature of 25° C., optionally neutralized and at a concentration by weight of 0.1%, make it possible to obtain a macroscopically homogeneous and transparent or translucent solution or suspension, i.e., having a light transmission value, at a wavelength equal to 500 nm, through a sample with a thickness of 1 cm, of at least, for example, 70%, and further, for example, of at least 80%.

The at least one linear block copolymer may, for example, be chosen from water-soluble copolymers, optionally in the neutralized form.

The concentration of the at least one linear block copolymer in the washing compositions disclosed herein may, for example, range from 0.01 to 20% by weight, and further, for example, range from 0.1 to 5% by weight, with respect to the total weight of the washing composition.

The at least one linear block copolymer disclosed herein can be prepared by the synthetic processes conventionally used to produce block polymers. Mention may be made, for example, of anionic or cationic polymerizations and controlled radical polymerization (see "New Method of Polymer Synthesis", Blackie Academic & Professional, London, 1995, volume 2, page 1, or Trends Polym. Sci., 4, page 183 (1996) by C. J. Hawker), wherein the controlled radical polymerization can be carried out according to different processes, for example, atom transfer radical polymerization (ATRP) (see JACS, 117, page 5614 (1995), by Matyjasezwski et al.), or the method of radicals, such as nitroxides (Georges et al., Macromolecules, 26, page 2987 (1993)).

The processes to produce just one of the two types of blocks of the at least one linear block copolymer disclosed herein can also be used, wherein the other block is introduced into the final polymer via the initiator used or by a coupling reaction between the at least one hydrophilic block and the at least one hydrophobic block.

The at least one polymer chosen from cationic and amphoteric polymers. used in the compositions disclosed herein, in combination with the at least one linear block copolymer described above can, for example, be chosen from synthetic polymers and polymers obtained by chemical modification of polysaccharides.

The cationic polymers may, for example, be chosen from those disclosed in Patent Application Nos. EP 0 337 354, FR 2 270 846, FR 2 383 660, FR 2 598 611, FR 2 470 596 and FR 2 519 863.

The cationic polymers may, for example, be chosen from polymers comprising units comprising at least one group chosen from primary, secondary, tertiary and quaternary amine groups, which may form part of the main macromolecular chain and/or may be carried by at least one side group directly connected to the main macromolecular chain.

The cationic polymers may, for example, be chosen from polymers of the polyquaternary amine type, polymers of the polyquaternary aminoamide type, and polymers of the polyquaternary ammonium type. These polymers are known products.

For example, the polymers of the polyquaternary amine, polyquaternary aminoamide and polyquaternary ammonium type which can be used in the compositions disclosed herein can be chosen from those polymers disclosed in French Patent Nos. 2 505 348 and 2 542 997.

For example, the synthetic cationic polymers may be chosen from polymers of the following families:
(1) homopolymers and copolymers of acrylic esters, methacrylic esters, acrylamides and methacrylamides comprising at least one amine functional group, comprising at least one unit of following formulae:

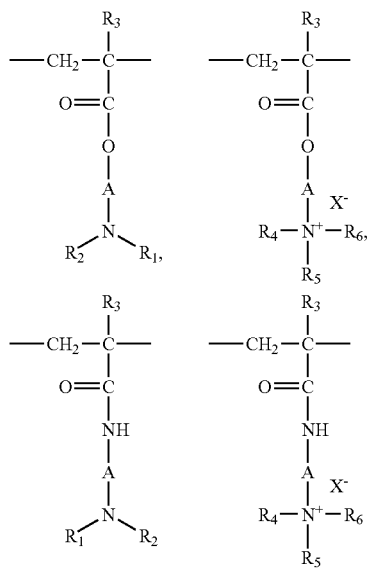

wherein:

$R_3$, which may be identical or different, is chosen from a hydrogen atom and a $CH_3$ group;

A, which may be identical or different, is chosen from linear and branched alkyl groups comprising from 1 to 6 carbon atoms, for example, 2 or 3 carbon atoms, and hydroxyalkyl groups comprising from 1 to 4 carbon atoms;

$R_4$, $R_5$ and $R_6$, which may be identical or different, are each chosen from alkyl groups comprising from 1 to 18 carbon atoms, a benzyl group, and, for example, alkyl groups comprising from 1 to 6 carbon atoms;

$R_1$ and $R_2$, which may be identical or different, are each chosen from a hydrogen atom and alkyl groups comprising from 1 to 6 carbon atoms, for example, methyl groups and ethyl groups;

$X^-$ is an anion chosen from anions derived from inorganic and organic acids, such as a methyl sulfate anion and halides, such as chloride and bromide.

The copolymers of the family (1) can further comprise at least one unit deriving from comonomers which may be chosen from acrylamides, methacrylamides, diacetone acrylamides, acrylamides and methacrylamides substituted on the nitrogen atom by at least one group chosen from lower $C_{1-4}$ alkyl groups, groups derived from acrylic and methacrylic acids and from their esters, vinyllactams, such as vinylpyrrolidone and vinylcaprolactam, and vinyl esters.

For example, the copolymers of the family (1) may be chosen from:

copolymers of acrylamide and of dimethylaminoethyl methacrylate which may be quaternized with dimethyl sulfate or with a dimethyl halide, such as that sold under the name Hercofloc® by Hercules, copolymers of acrylamide and of methacryloyloxyethyltrimethylammonium chloride, disclosed, for example, in Patent Application No. EP-A-080 976 and sold under the name Binaquat® P 100 by Ciba-Geigy, copolymers of acrylamide and of methacryloyloxyethyltrimethylammonium methyl sulfate sold under the name Reten® by Hercules, vinylpyrrolidone/dialkylaminoalkyl acrylate and methacrylate copolymers, which may or may not be quaternized, such as the products sold under the name Gafquat® by ISP, for example, Gafquat® 734 and Gafquat® 755, and the products named Copolymer 845, 958 and 937. These polymers are disclosed in detail in French Patent Nos. 2 077 143 and 2 393 573, dimethylaminoethyl methacrylate/vinylcaprolactam/vinylpyrrolidone terpolymers, such as the product sold under the name Gaffix® VC 713 by ISP, vinylpyrrolidone/methacrylamidopropyldimethylamine copolymers, sold, for example, under the name Styleze® CC 10 by ISP, and vinylpyrrolidone/quaternized dimethylaminopropylmethacrylamide copolymers, such as the product sold under the name Gafquat® HS 100 by ISP;

(2) Polymers comprising at least one piperazinyl unit and at least one unit chosen from alkylene and hydroxyalkylene units, wherein the alkylene and hydroxyalkylene units comprise at least one group chosen from straight- and branched-chain alkylene and hydroxyalkylene groups respectively, optionally interrupted by at least one entity chosen from oxygen, sulfur and nitrogen atoms, aromatic rings, and heterocyclic rings; and the oxidation and/or quaternization products of these polymers. Such polymers are disclosed, for example, in French Patent Nos. 2 162 025 and 2 280 361;

(3) Water-soluble polyaminoamides prepared, for example, by polycondensation of an acidic compound with a polyamine. These polyaminoamides can be crosslinked by at least one crosslinking agent chosen from epihalohydrins, diepoxides, dianhydrides, unsaturated dianhydrides, bisunsaturated derivatives, bishalohydrins, bisazetidiniums, bishaloacyldiamines, alkyl bishalides, and oligomers resulting from the reaction of a bifunctional compound reactive with respect to a bishalohydrin, a bisazetidinium, a bishaloacyldiamine, an alkyl bishalide, an epihalohydrin, a diepoxide and a bisunsaturated derivative; wherein the at least one crosslinking agent is used in an amount ranging from 0.025 to 0.35 mol per amine group of the polyaminoamide. These polyaminoamides can be alkylated or, if they comprise at least one tertiary amine functional group, they can be quaternized. Such polymers are disclosed, for example, in French Patent Nos. 2 252 840 and 2 368 508;

(4) Polyaminoamide derivatives resulting from the condensation of polyalkylenepolyamines with polycarboxylic acids, followed by an alkylation by bifunctional agents. The polyaminoamide derivatives may, for example, be chosen from adipic acid/dialkylaminohydroxyalkyl/dialkylenetriamine polymers wherein the alkyl group comprises from 1 to 4 carbon atoms and, for example, is chosen from methyl, ethyl and propyl groups and alkylene groups comprising from 1 to 4 carbon atoms and, for example, is chosen from ethylene groups. Such polymers are disclosed, for example, in French Patent No.1 583 363.

For example, the polyamidoamino derivatives may be chosen from adipic acid/dimethylaminohydroxypropyl/diethylenetriamine polymers sold under the name Cartaretine® F, F4 or F8 by Sandoz;

(5) Polymers obtained by reaction of a polyalkylenepolyamine comprising two primary amine groups and at least one secondary amine group with a dicarboxylic acid chosen from diglycolic acid and saturated aliphatic dicarboxylic acids comprising from 3 to 8 carbon atoms, wherein the molar ratio of the polyalkylenepolyamine to the dicarboxylic acid ranges from 0.8:1 to 1.4:1. The polyaminoamide resulting from this reaction is subsequently brought to react with epichlorohydrin in a molar ratio of epichlorohydrin in relation to the secondary amine group of the polyaminoamide ranging from 0.5:1 to 1.8:1. Such polymers are disclosed, for example, in U.S. Pat. Nos. 3,227,615 and 2,961,347.

For example, polymers of this type are sold under the name Hercosett® 57 by Hercules Inc. and under the name of PD 170 and Delsette® 101 by Hercules in the case of the adipic acid/epoxypropyl/diethylenetriamine copolymer;

(6) Cyclopolymers of alkyldiallylamine and of dialkyldiallylammonium, such as the homopolymers and copolymers comprising, as a main constituent of the chain, at least one unit chosen from units corresponding to the formulae (Va) and (Vb):

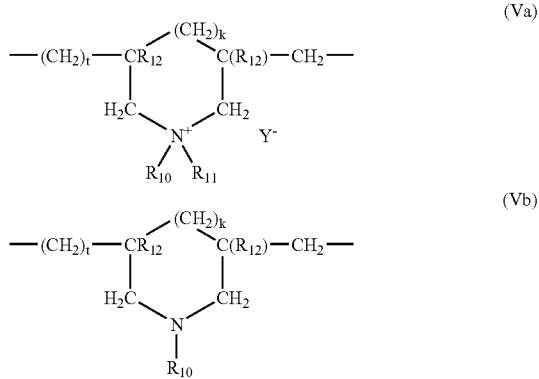

wherein:

k and t are each equal to 0 or 1, the sum k+t being equal to 1;

$R_{12}$, which may be identical or different, is chosen from a hydrogen atom and a methyl group;

$R_{10}$ and $R_{11}$, which may be identical or different, are each chosen from alkyl groups comprising from 1 to 6 carbon atoms, $C_{1-5}$ hydroxyalkyl groups, and lower $C_1$–$C_4$ amidoalkyl groups or $R_{10}$ and $R_{11}$ can form, together with the nitrogen atom to which they are attached, a heterocyclic group such as piperidinyl and morpholinyl;

Y⁻ is an anion chosen from bromide, chloride, acetate, borate, citrate, tartrate, bisulfate, bisulfite, sulfate and phosphate.

These polymers are disclosed, for example, in French Patent No. 2 080 759 and in its Certificate of Addition 2 190 406.

For example, the cyclopolymers of alkyldiallylamine and of diallylammonium may be chosen from the homopolymers of dimethyldiallylammonium chloride sold under the name Merquat® 100 by Nalco (and its homologs of low weight-average molecular masses) and the copolymers of diallyldimethylammonium chloride and of acrylamide sold under the name Merquat® 550;

(7) Diquaternary ammonium polymers comprising repeating units corresponding to the formula (VI):

wherein:

$R_{13}$, $R_{14}$, $R_{15}$ and $R_{16}$, which may be identical or different, are each chosen from aliphatic, alicyclic and arylaliphatic groups comprising from 1 to 20 carbon atoms; and lower aliphatic hydroxyalkyl groups or $R_{13}$, $R_{14}$, $R_{15}$ and $R_{16}$, together or separately, form, with the nitrogen atom to which they are attached, at least one heterocycle optionally comprising a second heteroatom other than nitrogen or $R_{13}$, $R_{14}$, $R_{15}$ and $R_{16}$, which may be identical or different, are each chosen from linear and branched $C_{1-6}$ alkyl groups substituted by at least one group chosen from nitrile, ester, acyl, amide, —CO—O—$R_{17}$-D and —CO—NH—$R_{17}$-D groups, wherein $R_{17}$, which may be identical or different, is chosen from alkylene groups and D, which may be identical or different, is chosen from quaternary ammonium groups;

$A_1$ and $B_1$, which may be identical or different, are each chosen from linear and branched, saturated and unsaturated polymethylene groups comprising from 2 to 20 carbon atoms, and which can comprise, bonded to or inserted into the main chain, at least one entity chosen from aromatic rings, oxygen and sulfur atoms, and sulfoxide, sulfone, disulfide, amino, alkylamino, hydroxyl, quaternary ammonium, ureido, amide and ester groups, and X⁻ is an anion chosen from anions derived from inorganic and organic acids;

$A_1$, $R_{13}$ and $R_{15}$ can form, with the two nitrogen atoms to which they are attached, a piperazine ring; in addition, if $A_1$ is chosen from linear and branched, saturated and unsaturated alkylene and hydroxyalkylene groups, $B_1$ can also be chosen from groups of the following formula:

$$-(CH_2)_n-CO-D-OC-(CH_2)_n-$$

wherein D is chosen from:

a) glycol residues of formula —O-Z-O—, wherein Z is chosen from linear and branched hydrocarbonaceous groups and groups corresponding to the following formulae:

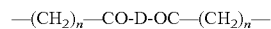

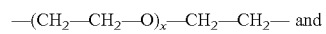

wherein x and y, which may be identical or different, are each chosen from integers ranging from 1 to 4, representing a defined and unique degree of polymerization, or any number ranging from 1 to 4 representing a mean degree of polymerization;

b) bissecondary diamine residues, such as piperazine derivatives;

c) bisprimary diamine residues of formula: —NH—Y—NH—, wherein Y is chosen from linear and branched hydrocarbonaceous groups and the divalent group —CH₂—CH₂—S—S—CH₂—CH₂—; and d) a ureylene group of formula —NH—CO—NH—; and n ranges from 1 to 100, such as from 1 to 50.

In one embodiment, for example, X⁻ is chosen from anions such as chloride and bromide.

These polymers have a number-average molecular mass which may range, for example, from 1 000 to 100 000.

These polymers are disclosed, for example, in French Patent Nos. 2 320 330, 2,270,846, 2,316,271, 2,336,434 and 2,413,907 and U.S. Pat. Nos. 2,273,780, 2,375,853, 2,388, 614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Further, polymers that comprise repeating units corresponding to the formula (VII) below can be used:

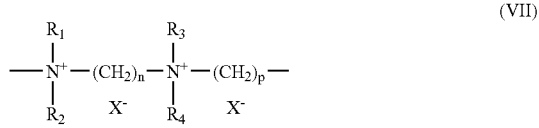

wherein $R_1$, $R_2$, $R_3$ and $R_4$, which may be identical or different, are each chosen from alkyl and hydroxyalkyl groups comprising from 1 to 4 carbon atoms; n and p, which may be identical or different, are each an integer chosen from integers ranging from 2 to 20; and $X^-$ is an anion chosen from anions derived from inorganic and organic acids.

For example, one polymer comprising repeating units of formula (VII) can be used in the compositions disclosed herein, wherein $R_1$, $R_2$, $R_3$ and $R_4$, are each a methyl group, n=3, p=6 and X=Cl, named Hexadimethrine chloride (CTFA);

(8) Polyquaternary ammonium polymers comprising units of formula (VIII):

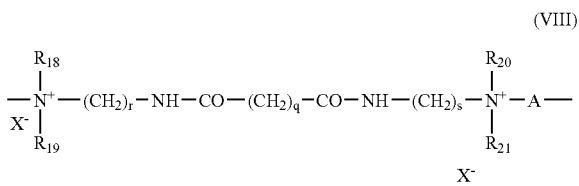

wherein:

$R_{18}$, $R_{19}$, $R_{20}$ and $R_{21}$, which may be identical or different, are each chosen from a hydrogen atom and methyl, ethyl, propyl, β-hydroxyethyl, β-hydroxypropyl and $—CH_2CH_2(OCH_2CH_2)_pOH$ groups, wherein p is equal to 0 or to an integer ranging from 1 to 6, provided that $R_{18}$, $R_{19}$, $R_{20}$ and $R_{21}$ do not simultaneously represent a hydrogen atom, r and s, which may be identical or different, are each an integer chosen from integers ranging from 1 to 6, q is equal to 0 or to an integer ranging from 1 to 34, $X^-$ is chosen from anions, such as halides, and A is chosen from divalent radicals, for example, a $—CH_2—CH_2—O—CH_2—CH_2—$ group.

Such polymers are disclosed, for example, in patent application No. EP-A-122 324.

The polyquaternary ammonium polymers comprising units of formula (VIII) may, for example, be chosen from the products Mirapol® A 15, Mirapol® AD1, Mirapol® AZ1 and Mirapol® 175, sold by Miranol.

(9) Quaternary polymers of vinylpyrrolidone and of vinylimidazole, for example, the products sold under the names Luviquat® FC 905, FC 550 and FC 370 by BASF. For example, the quaternary polymers of vinylpyrrolidone and of vinylimidazole may be chosen from copolymers of vinylpyrrolidone and of methylvinylimidazolium chloride.

(10) Polyamines, such as Polyquart® H sold by Henkel, which are referenced under the name of Polyethylene Glycol (15) Tallow Polyamine in the CTFA dictionary.

(11) Crosslinked and noncrosslinked polymers of methacryloyloxy($C_{1-4}$)alkyltri($C_{1-4}$)alkylammonium salts, such as the polymers obtained by homopolymerization of dimethylaminoethyl methacrylate quaternized by methyl chloride or by copolymerization of acrylamide and of dimethylaminoethyl methacrylate quaternized by methyl chloride, the homopolymerization or the copolymerization being followed by a crosslinking by a compound possessing olefinic unsaturation, for example, methylenebisacrylamide. It is also possible to use, for example, a crosslinked acrylamide/methacryloyloxyethyltrimethylammonium chloride (20/80 by weight) copolymer in the form of a dispersion comprising 50% by weight of said copolymer in mineral oil. This dispersion is sold under the name of Salcare® SC 92 by Ciba. It is also possible to use a crosslinked homopolymer of methacryloyloxyethyltrimethylammonium chloride comprising approximately 50% by weight of the homopolymer in mineral oil or in a liquid ester. These dispersions are sold under the names of Salcare® SC 95 and Salcare® SC 96 by Ciba.

The cationic polysaccharide polymers may, for example, be chosen from polymers of the following families:

(1) The cellulose ether derivatives comprising at least one quaternary ammonium group disclosed in French Patent No. 1 492 597, for example, the polymers sold under the "JR" (JR 400, JR 125, JR 30M) and "LR" (LR 400, LR 30M) names by Almerchol. These polymers are also defined in the CTFA dictionary as quaternary ammoniums of hydroxyethylcellulose having reacted with an epoxide substituted by a trimethylammonium group.

(2) Cationic derivatives of celluose, such as copolymers of cellulose and derivatives of cellulose which are grafted with at least one water-soluble quaternary ammonium monomer, and which are disclosed, for example, in U.S. Pat. No. 4,131,576, such as hydroxyalkylcelluloses, for example hydroxymethyl-, hydroxyethyl- and hydroxypropylcelluloses, grafted, for example, with at least one salt chosen from methacryloylethyltrimethylammonium, methacrylamidopropyltrimethylammonium and dimethyldiallylammonium salts.

The commercially available products corresponding to this definition are, for example, the products sold under the name Celquat® L 200 and Celquat® H 100 by National Starch.

(3) The cationic polysaccharides disclosed, for example, in U.S. Pat. Nos. 3,589,578 and 4,031,307, such as cationic guar gums, for example, comprising at least one trialkylammonium cationic group. The cationic polysaccharides may, for example, be chosen from guar gums modified by a 2,3-epoxypropyltrimethylammonium salt, for example, the chloride.

Such products are sold, for example, under the tradenames of Jaguar® C13 S, Jaguar® C 15, Jaguar® C 17 and Jaguar® C162 by Meyhall.

(4) Chitosans and the salts thereof, such as chitosan acetate, lactate, glutamate, gluconate and pyrrolidonecarboxylate.

For example, the chitosans and the salts thereof may be chosen from chitosans having a degree of deacetylation of 90.5% by weight sold under the name Kytan Brut Standard by Aber Technologies and the chitosan pyrrolidonecarboxylate sold under the name Kytamer® PC by Amerchol.

The synthetic amphoteric polymers may, for example, be chosen from:

(1) copolymers of dimethyldiallylammonium chloride and of acrylic acid, sold, for example, under the names Merquat® 280 and Merquat® 295 by Nalco;

(2) terpolymers of dimethyldiallylammonium chloride, of acrylamide and of acrylic acid, sold, for example, under the name Merquat® Plus 3330 by Nalco;

(3) terpolymers of acrylamidopropyltrimethylammonium chloride, of acrylamide and of 2-amidopropanesulfonic acid, sold, for example, under the name Bozequat® 4000 by Hoechst, and (4) terpolymers of methacrylamidopropyltrimethylammonium chloride, of methyl acrylate and of acrylic acid, sold, for example, under the name Merquat® 2001 by Nalco.

The amphoteric polymers derived from polysaccharides may, for example, be chosen from polymers of the following families:

(1) guar gums carrying at least one cationic group and at least one anionic group, wherein the at least one cationic group can, for example, be chosen from primary, secondary and tertiary amine groups, and ammonium, sulfonium and phosphonium groups, and the at least one anionic group can, for example, be chosen from carboxyl, sulfonate, sulfate, phosphate and phosphonate groups, prepared in accordance with the process disclosed in Patent Application No. EP 0 943 627;

(2) amphoteric derivatives of cellulose ethers, disclosed in international Patent Application No. WO 90/03779, comprising on average, per glucose unit, at least 0.1 group comprising at least one functional group chosen from amine and ammonium functional groups of formula (I) below and at least 0.1 group comprising at least one carboxyl functional group of formula (II) below:

—[(CH$_2$)$_m$—N$^+$R$^1$R$^2$]$_x$—R$^3$ (I)

—C$_n$H$_{2n}$—COO$^-$ (II)

wherein: m=2–4, n=1–3, x=0–3; R$^1$ and R$^2$, which may be identical or different, are each chosen from C$_{1-4}$ alkyl groups; and R$^3$ is chosen from —(CH$_2$)$_m$—NR$^1$R$^2$ and —(CH$^2$)$_m$—N$^+$R$^1$R$^2$R$^4$ groups wherein R$^4$ is chosen from C$_{1-4}$ alkyl groups and —C$_{n\ H2n}$—COO$^{-\ groups}$;

(3) polymers derived from chitosans comprising units corresponding to the following formulae:

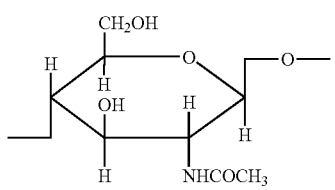

(A)

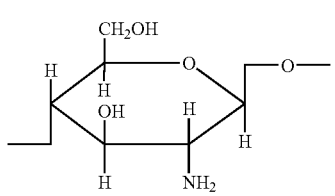

(B)

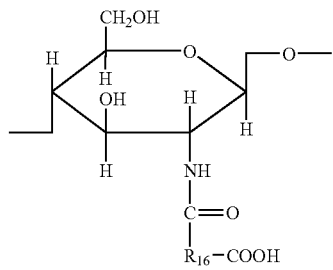

(C)

wherein the unit (A) is present in a proportion ranging from 0 to 30%, the unit (B) is in a proportion ranging from 5 to 50% and the unit (C) in a proportion ranging from 30 to 90%, wherein, in the unit (C), R$_{16}$ is chosen from groups of formula:

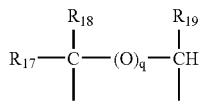

wherein, if q=0, R$_{17}$, R$_{18}$ and R$_{19}$, which may be identical or different, are each chosen from a hydrogen atom, methyl, hydroxyl, acetoxy and amino residues, monoalkylamino residues and dialkylamino residues, these residues being optionally interrupted by at least one nitrogen atom and/or optionally substituted by at least one entity chosen from amino, hydroxyl, carboxyl, alkylthio and sulfonic groups, and alkylthio residues wherein the alkyl group carries at least one amino residue, at least one of the R$_{17}$, R$_{18}$ and R$_{19}$ groups being, in this case, a hydrogen atom;

or, if q=1, R$_{17}$, R$_{18}$ and R$_{19}$, which may be identical or different, are each chosen from a hydrogen atom, and the acid and base addition salts thereof;

(4) Polymers obtained by N-carboxylation of chitosan, such as the N-carboxymethylchitosan and the N-carboxybutylchitosan sold under the name Evalsan® by Jan Dekker.

The at least one polymer chosen from cationic and amphoteric polymers disclosed herein may, for example, be film-forming polymers.

The at least one polymer chosen from cationic and amphoteric polymers may, for example, be present in the washing compositions disclosed herein in a concentration ranging from 0.001% to 20% by weight, further, for example, from 0.01 to 5% by weight, with respect to the total weight of the composition.

The combination of the two types of polymers for the compositions described above (at least one linear block copolymer+at least one polymer chosen from cationic and amphoteric polymers) is found in a specific base for washing compositions comprising the combination of at least one anionic surface-active agent and of at least one additional surface-active agent chosen from nonionic surface-active agents and amphoteric surface-active agents.

The anionic, nonionic and amphoteric surface-active agents which can be used in the compositions disclosed herein are known and commonly used in the cosmetics field.

For example, the at least one anionic surface-active agent which can be used in the compositions disclosed herein, can be chosen from salts, for example, alkali metal salts, such as sodium salts; ammonium salts; amine salts; aminoalcohol salts; alkaline earth metal salts, for example, magnesium salts, of the following types: alkyl sulfates, alkyl ether sulfates, alkylamido ether sulfates, alkylarylpolyether sulfates, monoglyceride sulfates; alkylsulfonates; alkylamidesulfonates; alkylarylsulfonates; α-olefinsulfonates; paraffinsulfonates; alkyl sulfosuccinates; alkyl ether sulfosuccinates; alkylamide sulfosuccinates; alkyl sulfoacetates; acylsarcosinates; and acylglutamates, wherein the alkyl and acyl groups of all these compounds comprise from 6 to 24 carbon atoms and the aryl groups may be chosen, for example, from a phenyl group and a benzyl group.

The at least one anionic surface-active agent may also be chosen, for example, from $C_{6-24}$ alkyl monoesters of polyglycosidedicarboxylic acids, such as alkyl glucosidecitrates, alkyl polyglycosidetartrates and alkyl polyglycosidesulfosuccinates, alkyl sulfosuccinamates, acylisethionates and N-acyltaurates, wherein the alkyl and acyl groups of all these compounds comprise from 12 to 20 carbon atoms.

The at least one anionic surface-active agent which can be used in the compositions disclosed herein may be chosen, for example, from acyllactylates, the acyl group of which comprises from 8 to 20 carbon atoms.

In addition, the at least one anionic surface-active agent can be chosen, for example, from alkyl-D-galactosideuronic acids and the salts thereof, and polyoxyalkylenated $(C_{6-24})$ alkyl ether carboxylic acids, polyoxyalkylenated $(C_{6-24})$ alkyl$(C_{6-24})$aryl ether carboxylic acids, polyoxyalkylenated $(C_{6-24})$alkylamido ether carboxylic acids and the salts thereof, for example, those comprising from 2 to 50 ethylene oxide units.

Further, for example, the at least one anionic surface active-agent may be chosen from alkyl sulfates, alkyl ether sulfates and alkyl ether carboxylates, for example, in the form of alkali metal and alkaline earth metal, ammonium, amine and aminoalcohol salts.

The amphoteric surface-active agents which can be used in the compositions disclosed herein can, for example, be chosen from derivatives of aliphatic secondary and tertiary amines wherein the aliphatic group is chosen from linear and branched chains comprising from 8 to 22 carbon atoms and comprising at least one anionic group, for example, at least one anionic group chosen from carboxylate, sulfonate, sulfate, phosphate and phosphonate groups. The amphoteric surface-active agents may be chosen, further, for example, from $(C_{8-20})$alkyl betaines, sulfobetaines, $(C_{8-20})$alkyl amido$(C_{6-8})$alkyl betaines and $(C_{8-20})$alkyl amido$(C_{6-8})$alkyl sulfobetaines.

For example, among the amine derivatives, the products sold under the name Miranol®, as disclosed in U.S. Pat. Nos. 2,528,378 and 2,781,354 and classified in the CTFA dictionary, 3rd edition, 1982, under the names Amphocarboxyglycinate and Amphocarboxypropionate, with the respective formulae (1) and (2) may be used in the compositions disclosed herein:

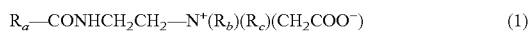

$$R_a\text{—CONHCH}_2\text{CH}_2\text{—N}^+(R_b)(R_c)(CH_2COO^-) \quad (1)$$

wherein:
$R_a$ is chosen from heptyl, nonyl and undecyl groups, and alkyl groups derived from an acid $R_a$—COOH present in hydrolyzed coconut oil,
$R_b$ is a β-hydroxyethyl group, and
$R_c$ is chosen from carboxymethyl groups;
and

$$R_a'\text{—CONHCH}_2\text{CH}_2\text{—N(B)(C)} \quad (2)$$

wherein:
B is chosen from —CH$_2$CH$_2$OX' groups,
C is chosen from —(CH$_2$)$_z$—Y' groups, wherein z=1 or 2,
X' is chosen from the —CH$_2$CH$_2$—COOH group and a hydrogen atom,
Y' is chosen from —COOH and —CH$_2$—CHOH—SO$_3$H groups, and
$R_a'$ is chosen from alkyl groups of an acid $R_a'$—COOH present in hydrolyzed linseed oil and coconut oil, and alkyl groups, for example, a $C_{17}$ alkyl group and its iso form, and an unsaturated $C_{17}$ alkyl group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caproamphodipropionate, lauroamphodipropionic acid and cocoamphodipropionic acid.

For example, the cocoamphodiacetate sold by Rhodia under the tradename Miranol® C2M concentrate may be used.

The amphoteric surface-active agents may, for example, be chosen from $(C_{8-20}$ alkyl$)$ betaines, $(C_{8-20}$ alkyl$)$ amido $(C_{6-8}$ alkyl$)$ betaines, and alkylamphodiacetates.

The nonionic surface-active agents which can be used in the compositions disclosed herein can be chosen from compounds well known per se (see, for example, "Handbook of Surfactants" by M. R. Porter, published by Blackie & Son (Glasgow and London), 1991, pp. 116–178). The nonionic surface-active agents are chosen, for example, from polyethoxylated, polypropoxylated and polyglycerolated fatty acids, $(C_{1-20})$alkylphenols, α-diols and alcohols comprising at least one fatty chain comprising, for example, from 8 to 18 carbon atoms, it being possible for the number of ethylene oxide or propylene oxide groups to range, for example, from 2 to 50 and it being possible for the number of glycerol groups to range, for example, from 2 to 30.

The nonionic surface-active agents may also, for example, be chosen from condensates of ethylene oxide and of propylene oxide with fatty alcohols; polyethoxylated fatty amides, for example, those comprising from 2 to 30 ethylene oxide units, polyglycerolated fatty amides comprising on average from 1 to 5 glycerol groups, for example, from 1.5 to 4 glycerol groups, sorbitan ethoxylated fatty acid esters comprising from 2 to 30 ethylene oxide units, sucrose fatty acid esters, polyethylene glycol esters of fatty acids, $(C_{6-24}$ alkyl$)$polyglycosides, N—$(C_{6-24}$ alkyl$)$glucamine derivatives, and amine oxides, such as oxides of $(C_{10-14}$ alkyl$)$ amines and N—$(C_{10-14}$ acyl$)$aminopropylmorpholine oxides.

The nonionic surface-active agents may also be chosen, for example, among the abovementioned nonionic surfactants, from $(C_{6-24}$ alkyl$)$polyglycosides.

The amount of the at least one anionic surface-active agent may range, for example, from 3% to 35% by weight, further, for example, from 5% to 25% by weight, with respect to the total weight of the composition.

The total amount of the at least one additional surface-active agent chosen from amphoteric and nonionic surface-active agents ranges, for example, from 0.5 to 30% by weight and further, for example, from 1 to 20% by weight, with respect to the total weight of the composition.

The pH of the washing compositions disclosed herein may, for example, range from 2 to 11 and further, for example, from 3 to 10.

The liquid medium of the compositions disclosed herein may be chosen from aqueous and aqueous/alcoholic mediums, i.e., in the latter case, the compositions comprise, in addition to an aqueous phase, at least one solvent chosen from lower alcohols, such as ethanol and isopropanol, and polyols, such as glycerol, propylene glycol and polyethylene glycols.

The compositions disclosed herein can further comprise at least one additive chosen from cosmetic active principles and formulation additives, such as natural and synthetic, anionic, amphoteric, zwitterionic, nonionic and cationic and associative and nonassociative polymeric thickeners, non-polymeric thickeners, such as acids and electrolytes, cationic surface-active agents, pearlescence agents, opacifying agents, dyes and pigments, fragrances, mineral, vegetable oils, synthetic oils, soluble, dispersible and insoluble silicones, waxes including ceramides, vitamins, UV screening agents, agents for combating free radicals, plasticizers, preservatives and pH-stabilizing agents.

A person skilled in the art will take care to choose the optional additives and their amounts so that they do not harm the advantageous properties of the compositions for washing keratinous fibers disclosed herein.

The compositions disclosed herein can optionally be provided in an aerosol form.

The embodiments disclosed herein are illustrated using the following examples, without, however, being limiting in nature.

EXAMPLE 1

The following two shampoos A and B were prepared:

|  | Shampoo A | Shampoo B |
|---|---|---|
| Sodium lauryl ether sulfate (2 EO) | 17% a.m. | 17% a.m. |
| Cocobetaine | 2.5% a.m. | 2.5% a.m. |
| JR 400[a)] | 0.25% | 0.5% |
| Cationic block copolymer[b)] | 0.25% | — |
| Water | q.s. for 100% | q.s. for 100% |

[a)] cellulose ether comprising quaternary ammonium groups sold by Amerchol
[b)] cationic block copolymer formed of a polystyrene block and of a poly (N-methyl-4-vinylpyridinium iodide) block sold by Polymer Source Inc (polystyrene (18 600 g/mol)-poly(N-methyl-4-vinylpyridinium iodide) (131 300 g/mol) diblock)
a.m. = active material Locks of natural hair were washed with each of the above shampoos and were subjected, after drying, to an evaluation by ten experts. Nine out of the ten experts found that the lock washed with shampoo A, according to the compositions disclosed herein, had a smoother feel and exhibited more body than the lock washed with shampoo B according to the state of the art.

EXAMPLE 2

A shampoo with the following composition was prepared:

| Sodium lauryl ether sulfate (2 EO) | 17% a.m. |
|---|---|
| Cocobetaine | 2.6% a.m. |
| JR 400 | 0.25% |
| Anionic block copolymer[a)] | 0.25% |
| Water | q.s. for 100% |

[a)] polystyrene-b-polyacrylic acid, 2 000 g/mol PS, 10 5000 g/mol PAA, sold under the reference P2476-SANa by Polymer Source Inc.

The composition had the same effects as those of composition A of example 1.

What is claimed is:

1. A composition for washing a keratinous substance comprising, in a cosmetically acceptable aqueous or aqueous/alcoholic medium,
   at least one linear block copolymer comprising at least one hydrophobic block and at least one hydrophilic block, wherein the at least one hydrophilic block is formed from anionic water-soluble monomers chosen from carboxylic acids comprising ethylenic unsaturation, 2-acrylamido-2-methylpropanesulfonic acid, styrenesulfonic acid, vinylsulfonic acid and vinylphosphonic acid,
   at least one polymer chosen from cationic and amphoteric polymers, and
   at least one anionic surface-active agent in combination with at least one additional surface-active agent chosen from nonionic surface-active agents and amphoteric surface-active agents.

2. The washing composition according to claim 1, wherein the keratinous substance is keratinous fibers.

3. The washing composition according to claim 1, wherein the at least one linear block copolymer, optionally neutralized, is dissolved or finely dispersed in the aqueous or aqueous/alcoholic medium.

4. The washing composition according to claim 3, wherein the at least one linear block copolymer, optionally neutralized, is soluble in water.

5. The washing composition according to claim 1, wherein the at least one hydrophobic block is formed from water-insoluble monomers chosen from at least one of vinylaromatic monomers, dienes and alkylated derivatives of dienes, chloroprene, $C_{1-10}$alkyl, $C_{6-10}$ aryl and $C_{7-20}$ aralkyl acrylates, $C_{1-10}$ alkyl, $C_{6-10}$ aryl and $C_{7-20}$ aralkyl methacrylates, vinyl acetate, vinyl ethers of formula $CH_2=CH-O-R$ and allyl ethers of formula $CH_2=CH-CH_2-O-R$ wherein R is chosen from $C_{1-6}$ alkyl groups, acrylonitrile, vinyl chloride, vinylidene chloride, caprolactone, ethylene, propylene, and fluorinated vinyl monomers and vinyl monomers comprising at least one perfluorinated chain.

6. The washing composition according to claim 1, wherein the at least one hydrophilic block comprises up to 25 mol % of water-insoluble monomers chosen from at least one of vinylaromatic monomers, dienes and alkylated derivatives of dienes, chloroprene, $C_{1-10}$ alkyl, $C_{6-10}$ aryl and $C_{7-20}$ aralkyl acrylates, $C_{1-10}$ alkyl, $C_{6-10}$ aryl and $C_{7-20}$ aralkyl methacrylates, vinyl acetate, vinyl ethers of formula $CH_2=CH-O-R$ and allyl ethers of formula $CH_2=CH-CH_2-O-R$ wherein R is chosen from $C_{1-6}$ alkyl groups, acrylonitrile, vinyl chloride, vinylidene chloride, caprolactone, ethylene, propylene, and fluorinated vinyl monomers and vinyl monomers comprising at least one perfluorinated chain.

7. The washing composition according to claim 6, wherein the at least one hydrophilic block comprises up to 10 mol % of at least one of the water-insoluble monomers.

8. The washing composition according to claim 7, wherein the at least one hydrophilic block comprises up to 5 mol % of at least one of the water-insoluble monomers.

9. The washing composition according to claim 1, wherein the at least one hydrophobic block comprises up to 25 mol % of at least one of water-soluble monomers chosen from anionic water-soluble monomers, nonionic water-soluble monomers, and cationic water-soluble monomers.

10. The washing composition according to claim 9, wherein the at least one hydrophobic block comprises up to 10 mol % of at least one of the water-soluble monomers.

11. The washing composition according to claim 10, wherein the at least one hydrophobic block comprises up to 5 mol % of at least one of the water-soluble monomers.

12. The washing composition according to claim 1, wherein the at least one linear block copolymer is present in a concentration ranging from 0.01 to 20% by weight, relative to the total weight of the composition.

13. The washing composition according to claim 12, wherein the at least one linear block copolymer is present in a concentration ranging from 0.1 to 5% by weight relative to the total weight of the composition.

14. The washing composition according to claim 1, wherein the cationic and amphoteric polymers are chosen from synthetic polymers and polymers obtained by chemical modification of polysaccharides.

15. The washing composition according to claim 14, wherein the cationic polymers are chosen from homopolymers and copolymers of acrylic esters, methacrylic esters, acrylamides and methacrylamides comprising at least one amine functional group; polymers comprising at least one unit chosen from piperazinyl units and at least one unit chosen from alkylene and hydroxyalkylene units; water-soluble polyaminoamides; cyclopolymers of alkyldiallylamine and of dialkyldiallylammonium; diquaternary ammonium polymers; polyquaternary ammonium polymers; quaternary polymers of vinylpyrrolidone and of vinylimidazole, polyamines; crosslinked and noncrosslinked polymers of methacryloyloxy($C_{1-4}$)alkyltri($C_{1-4}$)alkylammonium salts; cellulose ether derivatives comprising at least one quaternary ammonium group; cationic cellulose derivatives; cationic guar gums; and cationic chitosans.

16. The washing composition according to claim 14, wherein the amphoteric polymers are chosen from copolymers of dimethyldiallylammonium chloride and of acrylic acid; terpolymers of dimethyldiallylammonium chloride, of acrylamide and of acrylic acid; terpolymers of acrylamidopropyltrimethylammonium chloride, of acrylamide and of 2-amidopropanesulfonic acid; terpolymers of methacrylamido-propyltrimethylammonium chloride, of methyl acrylate and of acrylic acid; guar gums carrying at least one cationic group and at least one anionic group; amphoteric derivatives of cellulose ethers; and chitosans comprising at least one carboxyl group.

17. The washing composition according to claim 16, wherein the at least one cationic group is chosen from primary, secondary, and tertiary amine groups, ammonium groups, sulfonium groups, and phosphonium groups.

18. The washing composition according claim 16, wherein the at least one anionic group is chosen from carboxyl, sulfonate, sulfate, phosphate, and phosphonate groups.

19. The washing composition according to claim 1, wherein the cationic and amphoteric polymers are film-forming polymers.

20. The washing composition according to claim 1, wherein the at least one polymer chosen from cationic and amphoteric polymers is present in a concentration ranging from 0.001% to 20% by weight, relative to the total weight of the composition.

21. The washing composition according to claim 20, wherein the at least one polymer chosen from cationic and amphoteric polymers is present in a concentration ranging from 0.01 to 5% by weight, relative to the total weight of the composition.

22. The washing composition according to claim 1, wherein the at least one anionic surface-active agent is chosen from alkyl sulfates, alkyl ether sulfates and alkyl ether carboxylates.

23. The washing composition according to claim 22, wherein the at least one anionic surface-active agent is chosen from alkali metal, alkaline earth metal, ammonium, amine, and aminoalcohol salts of alkyl sulfates, alkyl ether sulfates, and alkyl ether carboxylates.

24. The washing composition according to claim 1, wherein the at least one anionic surface-active agent is present in a concentration ranging from 3 to 35% by weight, relative to the total weight of the composition.

25. The washing composition according to claim 24, wherein the at least one anionic surface-active agent is present in a concentration ranging from 5 to 25% by weight, relative to the total weight of the composition.

26. The washing composition according to claim 1, wherein the nonionic surface-active agents are chosen from ($C_{6-24}$ alkyl)polyglycosides.

27. The washing composition according to claim 1, wherein the amphoteric surface-active agents are chosen from at least one of ($C_{8-20}$ alkyl) betaines, ($C_{8-20}$ alkyl) amido($C_{6-8}$ alkyl) betaines, and alkylamphod iacetates.

28. The washing composition according to claim 1, wherein the total amount of the at least one additional surface-active agent chosen from amphoteric and nonionic surface-active agents ranges from 0.5 to 30% by weight, relative to the total weight of the composition.

29. The washing composition according to claim 28, wherein the total amount of the at least one additional surface-active agent chosen from amphoteric and nonionic surface-active agents ranges from 1 to 20% by weight, relative to the total weight of the composition.

30. A process for washing a keratinous substance comprising applying to the keratinous substance a composition comprising, in a cosmetically acceptable aqueous or aqueous/alcoholic medium, at least one linear block copolymer comprising at least one hydrophobic block and at least one hydrophilic block, wherein the at least one hydrophilic block is formed from anionic water-soluble monomers chosen from carboxylic acids comprising ethylenic unsaturation, 2-acrylamido-2-methylpropanesulfonic acid, styrenesulfonic acid, vinylsulfonic acid and vinylphosphonic acid at least one polymer chosen from cationic and amphoteric polymers, and at least one anionic surface-active agent in combination with at least one additional surface-active agent chosen from nonionic surface-active agents and amphoteric surface-active agents.

31. The process according to claim 30, wherein the keratinous substance are keratinous fibers.

* * * * *